United States Patent
Rhinier

(10) Patent No.: US 10,363,158 B1
(45) Date of Patent: Jul. 30, 2019

(54) ATHLETE FINGER GUARD

(71) Applicant: Jesse Rhinier, Hoboken, NJ (US)

(72) Inventor: Jesse Rhinier, Hoboken, NJ (US)

( * ) Notice: Subject to any disclaimer, the term of this patent is extended or adjusted under 35 U.S.C. 154(b) by 311 days.

(21) Appl. No.: 15/383,156

(22) Filed: Dec. 19, 2016

Related U.S. Application Data

(63) Continuation-in-part of application No. 14/617,142, filed on Feb. 9, 2015, now abandoned, which is a continuation-in-part of application No. 14/077,320, filed on Nov. 12, 2013, now abandoned.

(60) Provisional application No. 61/770,006, filed on Feb. 27, 2013.

(51) Int. Cl.
*A61F 5/01* (2006.01)
*A41D 13/08* (2006.01)
*A63B 71/14* (2006.01)

(52) U.S. Cl.
CPC .......... *A61F 5/013* (2013.01); *A41D 13/087* (2013.01); *A63B 71/14* (2013.01); *A61F 2005/0165* (2013.01); *A61F 2005/0181* (2013.01)

(58) Field of Classification Search
CPC .. A61F 5/00; A61F 5/01; A61F 5/0118; A61F 5/03; A61F 5/058; A61F 5/05866; A61F 5/05875; A61F 5/10; A41D 19/015; A41D 13/08; A41D 13/087; A63B 71/14
USPC ............ 602/21, 22; 2/16, 21, 22, 161.1, 163
See application file for complete search history.

(56) References Cited

U.S. PATENT DOCUMENTS

| | | | |
|---|---|---|---|
| 4,103,682 A | 8/1978 | Franzl | |
| 4,243,026 A | 1/1981 | Barber | |
| 4,441,489 A * | 4/1984 | Evans | A61F 5/10 602/22 |
| D291,830 S | 9/1987 | Murtaugh, III et al. | |
| D293,379 S | 12/1987 | Link | |
| D310,883 S | 9/1990 | Ellis | |
| 5,147,285 A * | 9/1992 | Buxton | A61F 5/013 602/16 |
| 5,197,943 A | 3/1993 | Link | |
| 5,232,436 A | 8/1993 | Janevski | |
| 6,110,136 A | 8/2000 | Belkin | |
| 6,716,186 B1 | 4/2004 | Singh et al. | |
| 6,932,782 B2 | 8/2005 | Ferraioli | |
| 7,169,121 B2 | 1/2007 | Berrehail | |
| 8,246,560 B2 * | 8/2012 | Gaylord | A61F 5/0118 602/21 |
| 8,381,313 B2 * | 2/2013 | Logan | A41D 13/087 2/21 |

(Continued)

*Primary Examiner* — Gloria M Hale
(74) *Attorney, Agent, or Firm* — Goldstein Law Offices, P.C.

(57) ABSTRACT

A guard for protecting a finger without interfering with athletic performance, having a rigid core that protects the finger from hyperextension and impact injuries. The guard has a proximal segment and a distal segment, each having a top surface, and a hinge assembly attached and extending above the top surfaces of the distal segment and proximal segment. The hinge assembly allows the distal segment to vary in position between a minimum position and a maximum position while remaining out of the way of adjacent fingers. The guard securely engages the finger by a distal strap that secures to a distal part of the finger, and a proximal strap that secures to a proximal part of the finger. The proximal part has sides that extend alongside the finger, and the distal segment only extends along the superior surface of the finger toward but not reaching the fingertip.

14 Claims, 10 Drawing Sheets

(56) References Cited

U.S. PATENT DOCUMENTS

2008/0196135 A1\* 8/2008 Gait ................ A41D 19/01588
                                                    2/21

\* cited by examiner

ATHLETE FINGER GUARD

CROSS-REFERENCE TO RELATED APPLICATIONS

This application is a continuation-in-part of utility patent application Ser. No. 14/617,142, filed in the United States Patent Office on Feb. 9, 2015, now abandoned, which is a continuation-in-part of utility patent application Ser. No. 14/077,320, filed in the United States Patent Office on Nov. 12, 2013, now abandoned, which is a nonprovisional utility application of provisional patent application Ser. No. 61/770,006, filed in the United States Patent Office on Feb. 27, 2013 and claims the priority thereof and is expressly incorporated herein by reference in its entirety.

TECHNICAL FIELD

The present disclosure relates generally to a finger guard. More particularly, the present disclosure relates to a guard for protecting a finger while participating in athletic activities.

BACKGROUND

During participation in athletic activities, whether at scholastic, amateur or professional levels, injuries occur. These injuries are often temporarily disabling and even if the injury does not impact the activities of daily living, they often inhibit participation and performance in athletic activities.

The injuries are often not severe enough to prevent the athlete from attempting to participate. Participants continue to participate, often times causing further injury.

In particular, when playing ball sports such as baseball, volleyball, football and basketball, participants sustain injuries to their fingers. When these digits are bandaged to prevent further injury and to promote proper healing, the bandaging inhibits performance in these sports because the participant cannot properly grip the ball or perform other actions. Traditional guards that rigidly maintain a digit in a straight linear manner, generally covering a fingertip particularly interfere with ball playing. Often if the participant uses such a device, it causes injury to other participants if there is contact. Less protective devices leave the digit open to re-injury during ball play.

Most guards known in the prior art are meant for fully immobilizing the finger for healing, and not for promoting athletic performance, and thus rigidly maintain the injured finger in a straight, linear position. These well-known devices cover a fingertip and inferior surface of the injured finger, thereby inhibiting the wearer from gripping equipment such as a ball during participation in athletic activities, such as baseball, volleyball, basketball and football, thereby negatively affecting performance. Additionally, the more protective the straight linear guard is, the more likely it is to cause injury to another participant during athletic activities. Other guards known in the prior art fail to provide the protection needed for participation in athletic activities.

While these units may be suitable for the particular purpose employed, or for general use, they would not be as suitable for the purposes of the present disclosure as disclosed hereafter.

In the present disclosure, where a document, act or item of knowledge is referred to or discussed, this reference or discussion is not an admission that the document, act or item of knowledge or any combination thereof was at the priority date, publicly available, known to the public, part of common general knowledge or otherwise constitutes prior art under the applicable statutory provisions; or is known to be relevant to an attempt to solve any problem with which the present disclosure is concerned.

While certain aspects of conventional technologies have been discussed to facilitate the present disclosure, no technical aspects are disclaimed and it is contemplated that the claims may encompass one or more of the conventional technical aspects discussed herein.

BRIEF SUMMARY

An aspect of an example embodiment in the present disclosure is to provide a guard for a finger that does not interfere with athletic performance and does not interfere with gripping a ball. Accordingly, an aspect of an example embodiment in the present disclosure provides a guard that engages only the superior surface of a finger, allowing the inferior surface of the injured digit to perform such actions as gripping a ball.

Another aspect of an example embodiment in the present disclosure is to provide a guard for a finger that allows controlled bending of the finger. Accordingly, a hinge is provided between the proximal and distal portions of the core to allow bending of the finger while preventing lateral forces from influencing the finger joints during such bending movements.

It is a further aspect of an example embodiment in the present disclosure to provide a guard for a finger that does not create additional bulkiness that might interfere with the performance of adjacent fingers. Accordingly, the hinge is located above the top surface of the guard—minimizing bulk along the sides of the finger.

A further aspect of an example embodiment in the present disclosure is to provide a guard that minimizes bulk while maximizing protection of the finger from extreme hits and forces during athletic performance such as playing ball sports. Accordingly, the present disclosure provides a guard with a rigid core and a padding element that protects the injured digit from further injury during athletic performance such as playing ball sports. Also, while the proximal segment has protective sides for securely anchoring to the finger, the distal segment only covers the top of the finger. In addition, a superior rib on the distal segment adds the strength needed to endure significant impacts, while still minimizing bulk to the distal segment.

It is yet another aspect of an example embodiment in the present disclosure to provide a guard that is adjustable to different finger widths. Accordingly, a rear fork allows slight lateral expansion and retraction of the proximal portion of the guard to accommodate different finger sizes.

The present disclosure describes a guard for protecting a finger without interfering with athletic performance, having a rigid core that protects the finger from hyperextension and impact injuries. The guard has a proximal segment and a distal segment, each having a top surface, and a hinge assembly attached and extending above the top surfaces of the distal segment and proximal segment. The hinge assembly allows the distal segment to vary in position between a minimum position and a maximum position while remaining out of the way of adjacent fingers. The guard securely engages the finger by a distal strap that secures to a distal part of the finger, and a proximal strap that secures to a proximal part of the finger. The proximal part has sides that extend alongside the finger, and the distal segment only extends along the superior surface of the finger toward but not reaching the fingertip to avoid interference to performance in ball sports.

The present disclosure addresses at least one of the foregoing disadvantages. However, it is contemplated that the present disclosure may prove useful in addressing other problems and deficiencies in a number of technical areas. Therefore, the claims should not necessarily be construed as limited to addressing any of the particular problems or deficiencies discussed hereinabove. To the accomplishment of the above, this disclosure may be embodied in the form illustrated in the accompanying drawings. Attention is called to the fact, however, that the drawings are illustrative only. Variations are contemplated as being part of the disclosure.

BRIEF DESCRIPTION OF THE DRAWINGS

In the drawings, like elements are depicted by like reference numerals. The drawings are briefly described as follows.

The present disclosure now will be described more fully hereinafter with reference to the accompanying drawings, which show various example embodiments. However, the present disclosure may be embodied in many different forms and should not be construed as limited to the example embodiments set forth herein. Rather, these example embodiments are provided so that the present disclosure is thorough, complete and fully conveys the scope of the present disclosure to those skilled in the art.

DETAILED DESCRIPTION OF THE PREFERRED EMBODIMENTS

Figure 6:
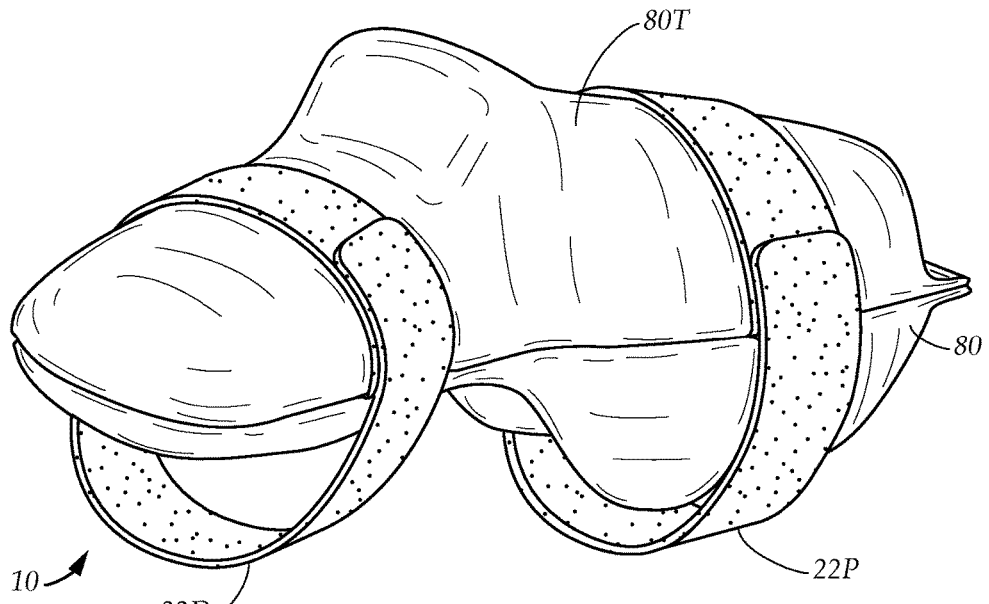
FIG. 6 is a diagrammatic perspective illustrating the guard, fully assembled.
Figure 7:
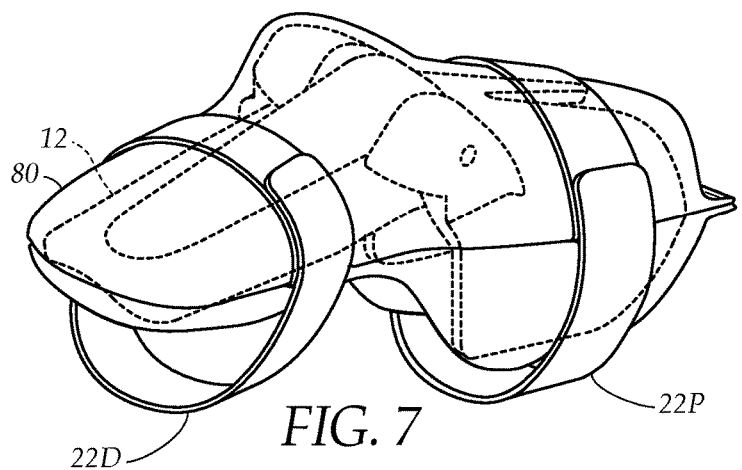
FIG. 7 is a diagrammatic perspective view of the guard, similar to FIG. 6, except wherein the core is indicated in phantom lines, depicting its position within the sheath.

FIGS. 6 and 7 illustrate a guard 10 for protecting a finger, while allowing finger mobility and usage during game play, to allow a player to effectively grasp a ball or other game equipment while playing sports. The guard 10 has a generally rigid guard core 12 located within a sheath 80 having a sheath top 80T, which is made of fabric or the like, and substantially encloses the core 12 such that contact between the finger and guard core 12 occurs through the sheath 80. The guard 10 has a proximal strap 22P and a distal strap 22D for securing the sheath 80 to the user.

Figure 2A:
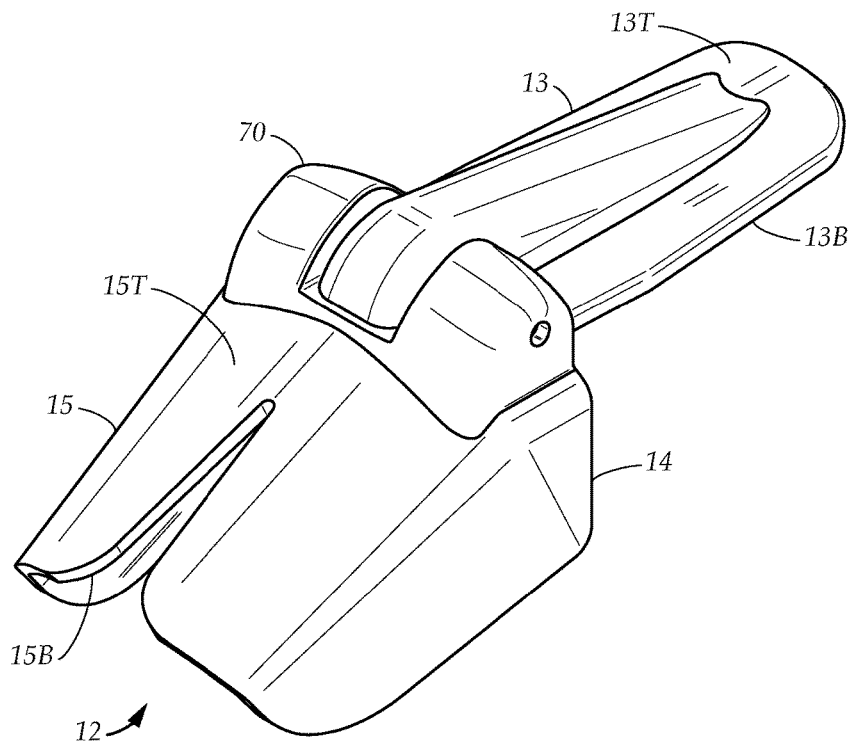
FIG. 2A is a diagrammatic perspective view of the core, viewed from the proximal end, with the distal segment at its maximum position.
Figure 2B:
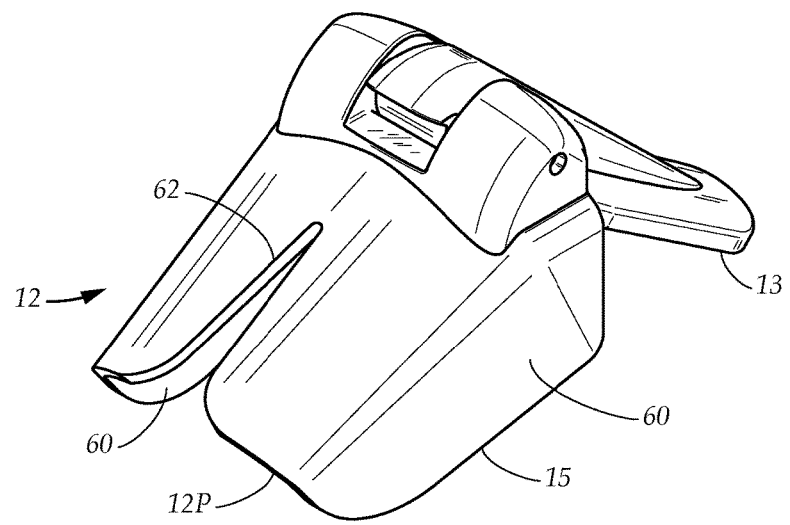
FIG. 2B is a diagrammatic perspective view of the core, viewed from the proximal end, with the distal segment at its minimum position.
Figure 3A:
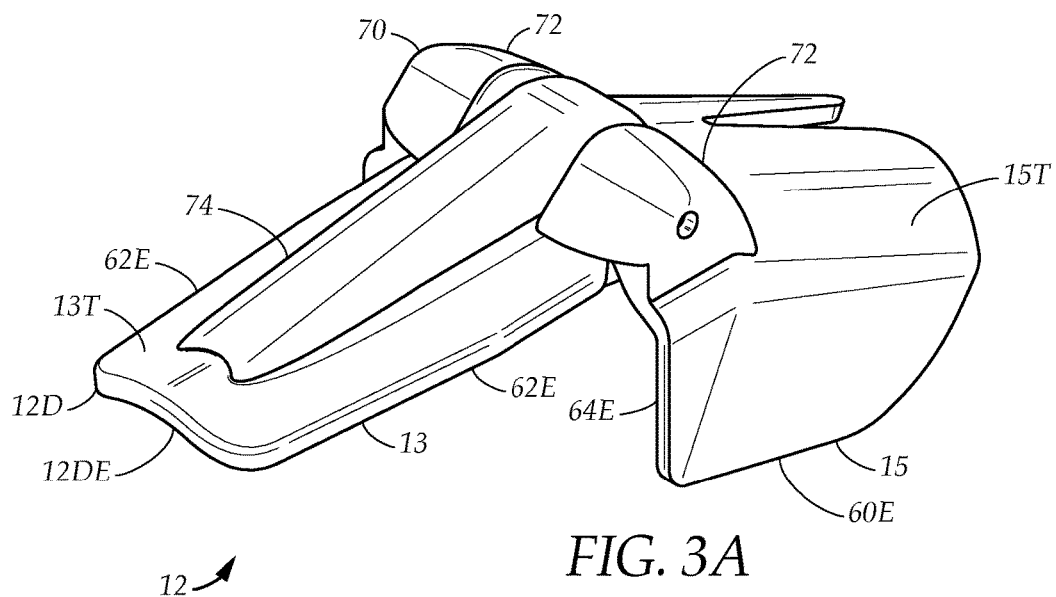
FIG. 3A is a diagrammatic perspective view of the core, viewed from the distal end, with the distal segment at its maximum position.
Figure 3B:
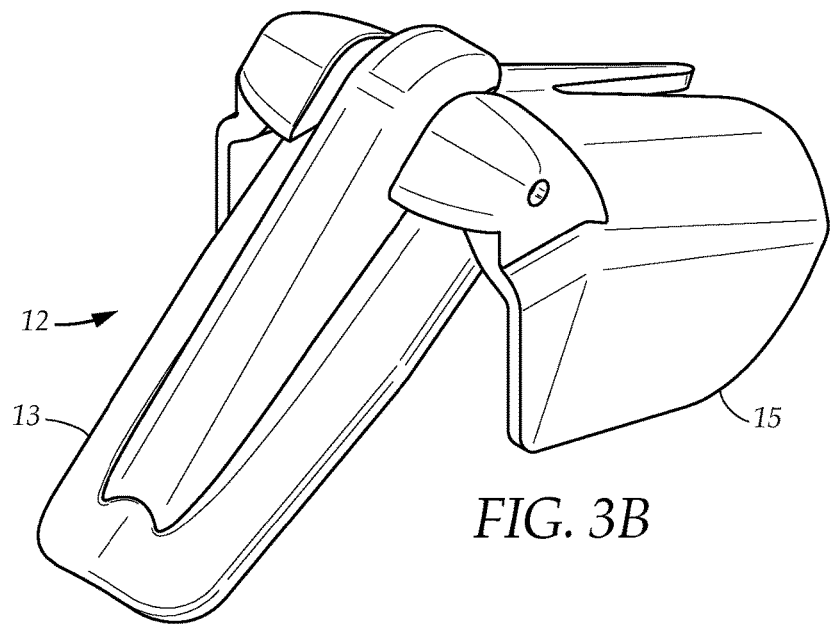
FIG. 3B is a diagrammatic perspective view of the core, viewed from the distal end, with the distal segment at its minimum position.

Referring to FIGS. 2A, 2B, 3A, and 3B, the core 12 has a distal segment 13 and a proximal segment 15. The proximal segment 15 has a middle segment 14 closest to the distal segment 13. The proximal segment 15 and distal segment 13 are formed from a rigid, impact-resistant material such ABS plastic. The proximal segment 15 has a top surface 15T and a bottom surface 15B; and the distal segment 13 has a top surface 13T and a bottom segment 13B. The distal segment 13 is hingedly attached to the proximal segment 15 by a hinge assembly 70 that is attached to and extends upwardly from the top surfaces 13T, 15T. The hinge assembly 70 allows for adjustment of the relative angle of the distal segment 13 and proximal segment 15 as the finger is bent, between a maximum position and a minimum position. At the maximum position, as illustrated in FIGS. 2B and 3B, the distal segment 13 is still biased toward the bottom segment at an obtuse angle. The obtuse angle is approximately the angle of the natural bend of a finger when gripping or grasping a ball, and thus the guard 10 prevents the finger from fully straightening, as a full straightened/locked finger is more susceptible to injury. The hinge assembly 70 also allows the finger to bend considerably, by allowing the distal segment 13 to reach the minimum position as shown in FIGS. 2A and 3A.

Figure 1:
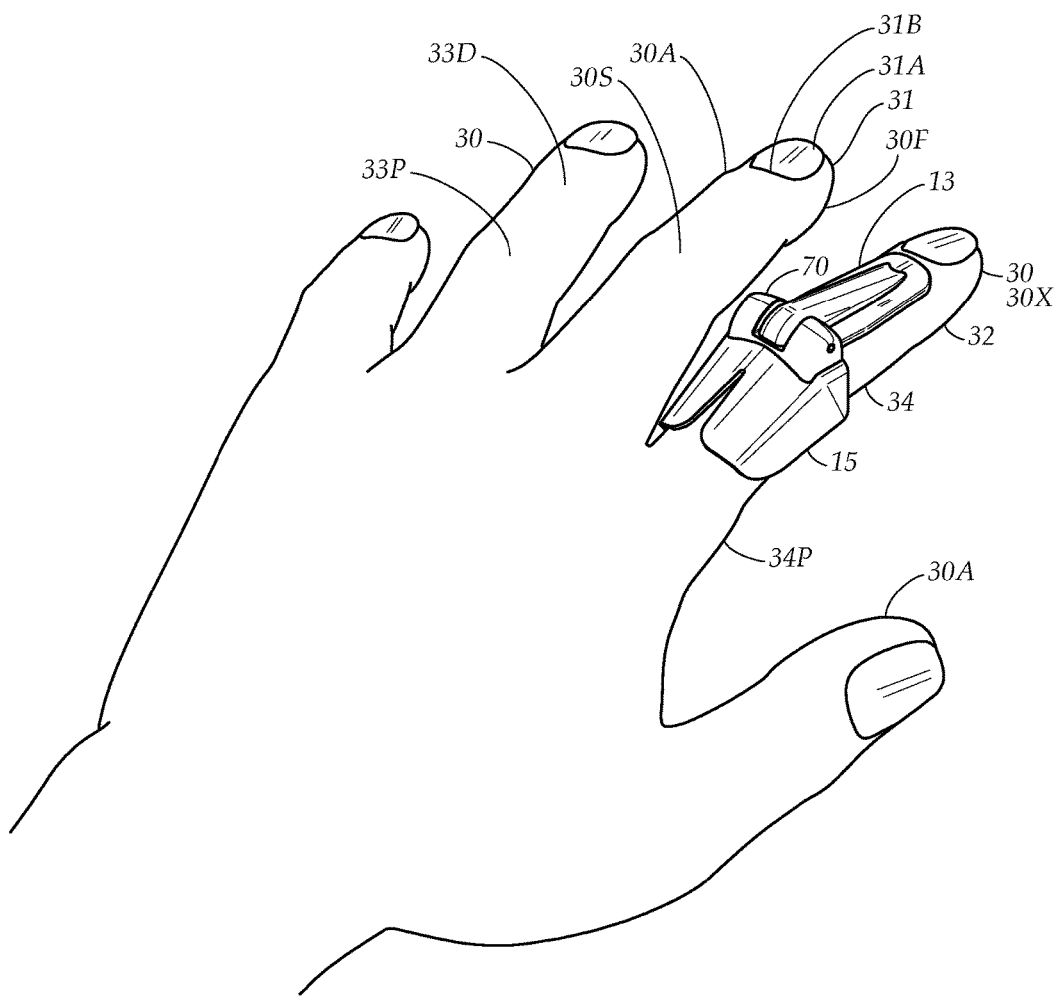
FIG. 1 is a diagrammatic perspective view of a core of the guard of the present disclosure, positioned on a finger of the user.
Figure 10:
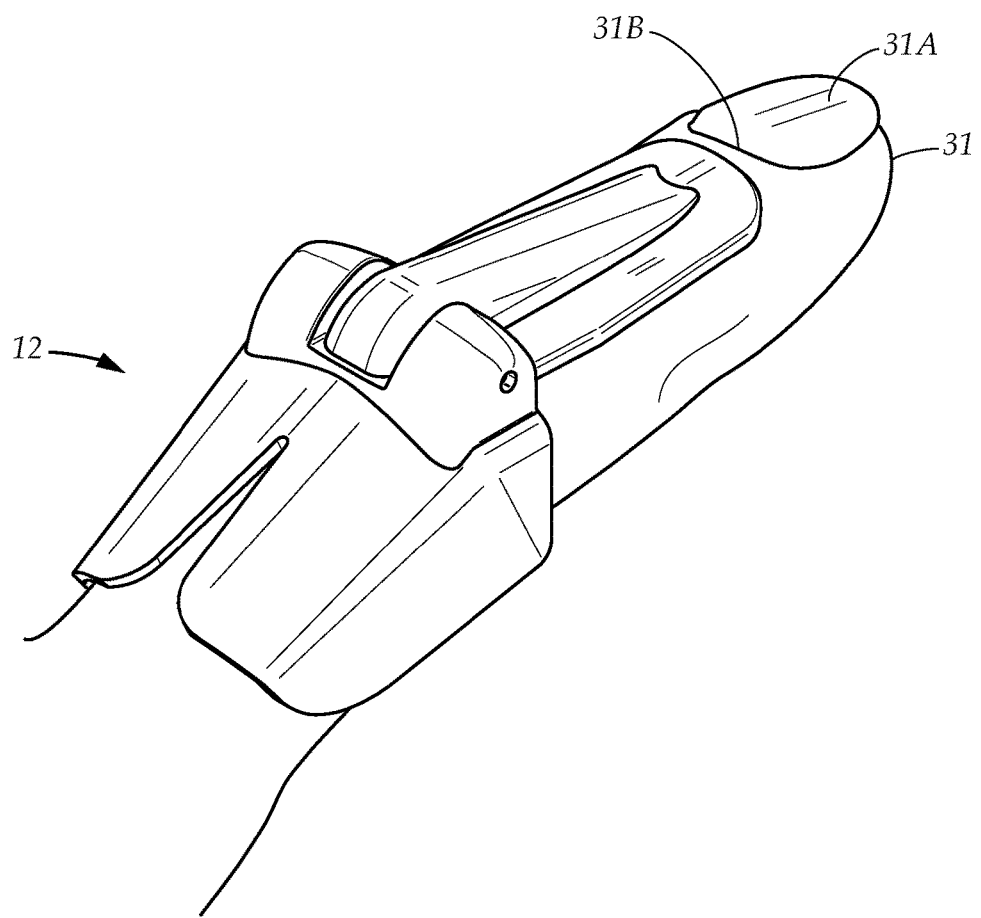
FIG. 10 is a diagrammatic perspective view, illustrating the core positioned on a finger.
Figure 11:
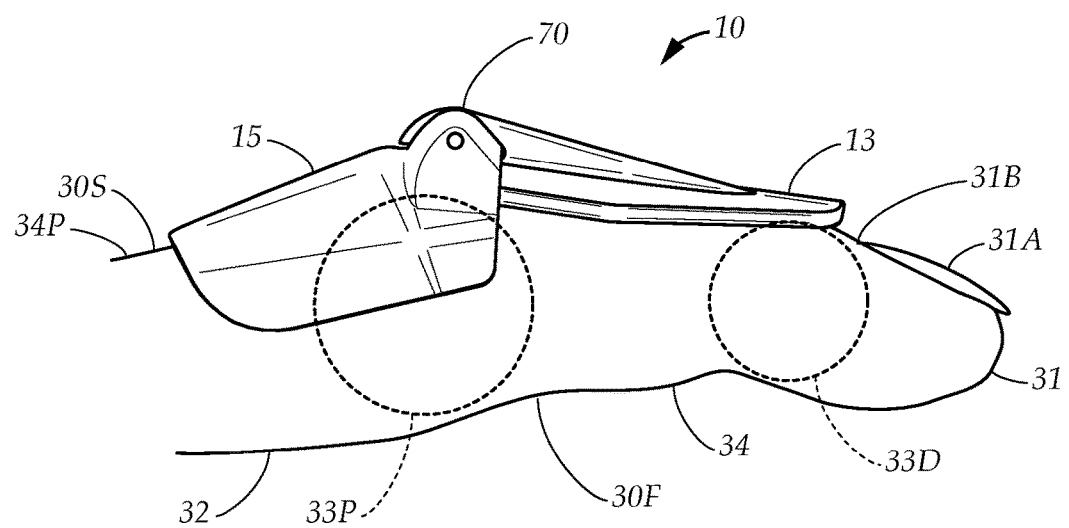
FIG. 11 is a side elevational view, illustrating the core in relation to the proximal interphalangeal joint (abbreviated as "PIP") and distal interphalangeal joint (abbreviated as "DIP") joints of the finger (indicated in phantom lines).
Figure 12:
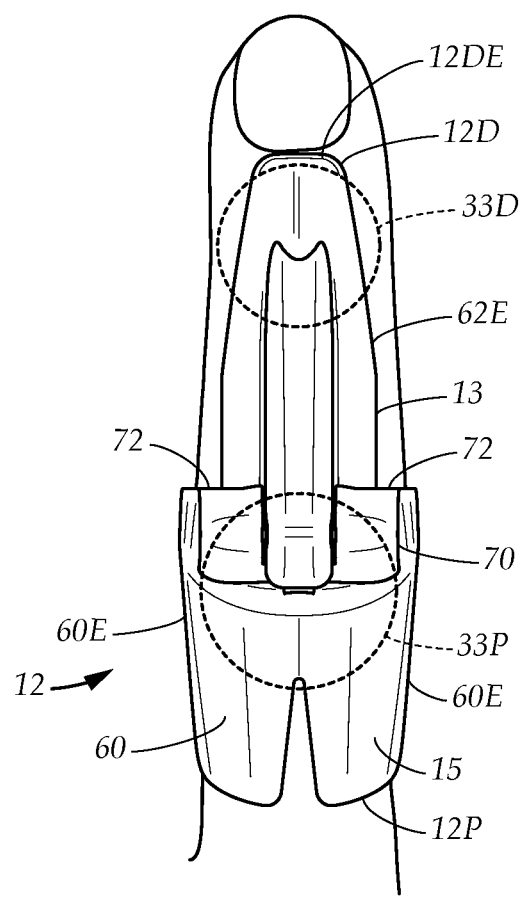
FIG. 12 is a top plan view, further illustrating the core in relation to the PIP and DIP joints of the finger (indicated in phantom lines).

FIG. 1 shows a hand 28 of an athlete, having a plurality of fingers 30, including an index finger 30X and adjacent fingers 30A alongside the index finger 30X. Each finger 30 having a superior surface 30S, an inferior surface 30F, a proximal part 34 having a proximal end 34P, a distal part 32 having a fingertip 31 with a finger nail 31A extending from the fingertip 31 and a nail bed 31B at a proximal end of the fingernail 31A. Referring to FIGS. 1 and 11, the finger 30 also having a proximal interphalangeal joint, also referred to as a "PIP" joint 33P, between the proximal part 34 and distal part 32, and a distal interphalangeal joint, also referred to as a "DIP" joint 33D, on the distal part 32 that is closer to the fingertip 31 than the PIP joint 33P. The guard 10 is shown secured to the index finger. The superior surface 30S of the finger extends against the guard 10 with the distal segment 13 of the guard coupled to the distal part 32 of the finger and the proximal segment 15 of the guard coupled to the proximal part 34 of the finger. Note that the hinge assembly 70 is elevated significantly above the superior surface 30S so that it does not interfere with the adjacent fingers 30A. Referring to FIGS. 11 and 12, the hinge assembly 70 is located slightly forward/distal of the PIP joint 33P, to ensure that the finger can bend significantly to positions desired for grasping a plurality of equipment, such as balls during participation in sports and other athletic activities. The inferior side of the finger 30F is unencumbered and unobstructed. Referring also to FIG. 10, the distal segment 15 of the guard core 12 ends near the nail bed 31B, without covering the fingernail 31A or extending to or beyond the fingertip 31.

Figure 4:
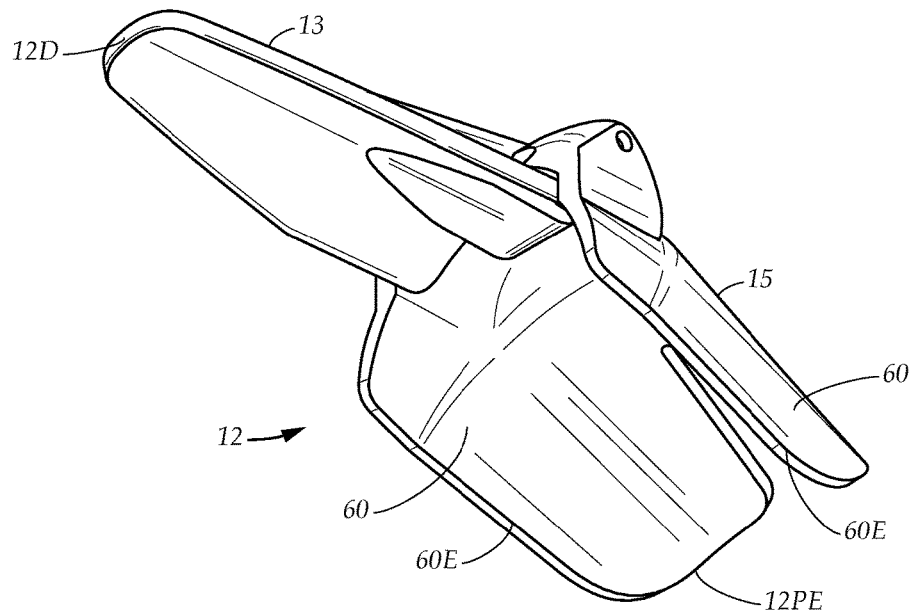
FIG. 4 is a diagrammatic perspective view of the core, viewed from underneath.

FIG. 4 and FIG. 12 illustrate the guard core 12 having a proximal end 12P having a proximal end edge 12PE and a distal end 12D having a distal end edge 12DE. The proximal segment 15 is significantly wider than the distal segment 13, having side extensions 60 that extend and curve transversely downwardly toward rear side edges 60E and wrap partially around the proximal part 34 of the finger without covering the inferior surface 30F of the finger 30 (as seen in FIG. 14A), such that the side extensions 60 substantially oppose each other at the rear side edges 60E. In contrast, the distal segment 13 is relatively narrow, and does not have sides as it is not intended to extend around the finger, as will be discussed further hereinbelow.

Referring to FIG. 2B, a fork split 62 partially bifurcates the proximal segment 15, extending proximally from near the hinge assembly 70 toward the proximal end 12P. The fork split 62, coupled with a slight flexibility of the guard core 12—allows the side extensions 60 to spread slightly or retract inwardly (substantially in the range of several millimeters) to allow different width fingers to be accommodated therebetween. Note then that while the guard core 12 may be generally described as rigid, it is pliable enough to spread laterally adjacent to the split. The split 62 is itself tapered, extending wider near the proximal end 12P, curving into the proximal end edge 12PE, and narrowing toward an apex 63 near the hinge assembly 70.

Referring to FIG. 3A, the distal segment 13 has forward side edges 62E that extend from the distal end edge 12DE and taper to extend slightly wider toward the proximal segment 15 than at the distal end 12D. Note that proximal segment 15 has middle side edges 64E that transition from the wider rear side edges 60E to substantially the width of the hinge assembly 70.

Figure 5:
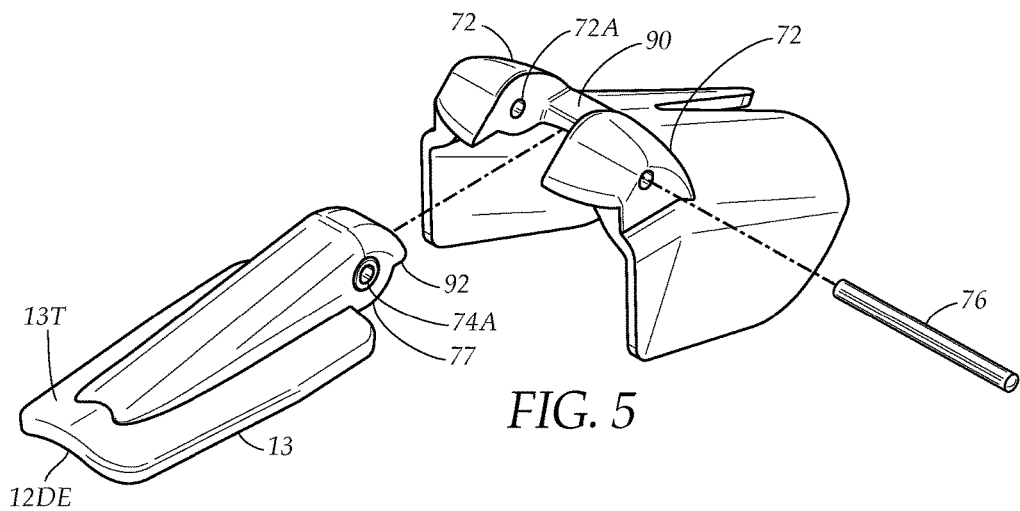
FIG. 5 is an exploded view of the core, illustrating details of the hinge assembly.

The hinge assembly 70 is configured to allow the distal segment 13 to flex with respect to the proximal segment 15, between the minimum position shown in FIGS. 2B and 3B, to the maximum position shown in FIGS. 2A and 3A. The hinge assembly 70 includes a pair of brackets 72 attached to the top surface 15T of the proximal segment 15, and a fin rib 74 attached to the top surface 13T of the distal segment 13. Referring to FIG. 5, the fin rib 74 has a knuckle 77 extending beyond the top surface 13T of the distal segment 13, and fully opposite from the distal end edge 12DE. The brackets 72 are joined by a substantially flat bridge surface 90 that is also raised above the top surface 15T of the proximal segment 15. The bridge surface 90 extends laterally between the brackets 72. The brackets 72 and fin rib 74 have transverse bores 72A, 74A. When the transverse bores 72A, 74A are aligned, a hinge pin 76 extends through the transverse bores 72A, 74A and thereby allows relative movement of the distal segment 13 with respect to the proximal segment 15, pivotally around said hinge pin 76. Note that the fin rib 74 has a tongue 92 on the knuckle 77 that extends over the bridge surface 90 of the proximal segment 15 and between the brackets. Accordingly, the tongue 92 limits pivotal motion of the distal segment 13 by the tongue 92 contacting the bridge surface 90 of the proximal segment 15 when the distal segment is at the maximum position to thereby prevent the distal segment 13 from moving beyond its maximum position. Note that at the maximum position, the distal segment 13 still forms an obtuse angle with the proximal segment 15, as seen in FIG. 11. Accordingly, this range of motion limit helps prevent further injury to the finger, by preventing hyperextension of the finger, and even prevent the finger from locking in a fully straight position where it would be especially prone to injury. Referring momentarily to FIG. 12, even at their widest, the forward side edges 62E of the distal segment 13 are narrower than the brackets 72 of the hinge assembly 70.

Figure 8:
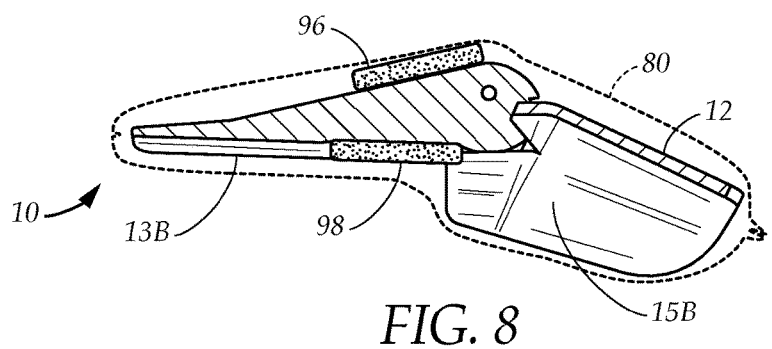
FIG. 8 is a side elevational view with parts broken away, illustrating upper an lower pads extending between the core and sheath.

Referring to FIG. 8, to help cushion the finger against hinge assembly within the guard core 12 as the finger bends, and further protect against impact and in particular against transmission of impact shock to the finger, an upper pad 96 and a lower pad 98 are provided immediately above and below the hinge assembly 70. In particular, the lower pad 98 is provided under the hinge against the bottom surfaces 13B, 15B of the distal and proximal segments 13, 15, but only extends in a region near where the proximal segments 13 and distal segments 15 meet. In actuality, the pads 96, 98, extend between the guard core 12 and the sheath 80, but the pads 98 provide impact protection that ensures that the guard 10 can be worn comfortably over long periods of time, for allowing extended game play.

Figure 9:
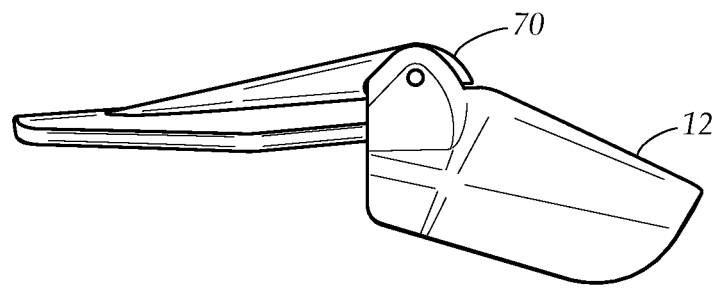
FIG. 9 is a side elevational view, illustrating several variations of the core, for accommodating different sized fingers.
Figure 9:
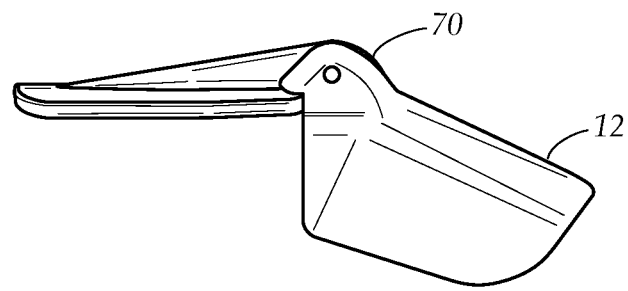
Figure 9:
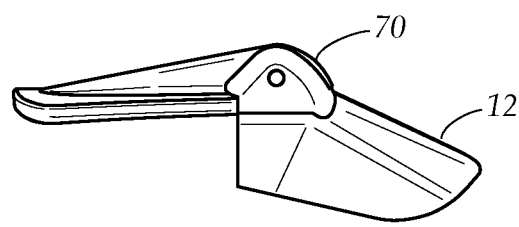

FIG. 9 illustrates several embodiments of the guard core 12. In particular, the guard core 12 is preferably provided is various sizes to ensure that the geometry of the core 12 matches the finger with which it is used, so that the hinge assembly 70 can be correctly positioned with respect to the finger as described above.

Figure 13:
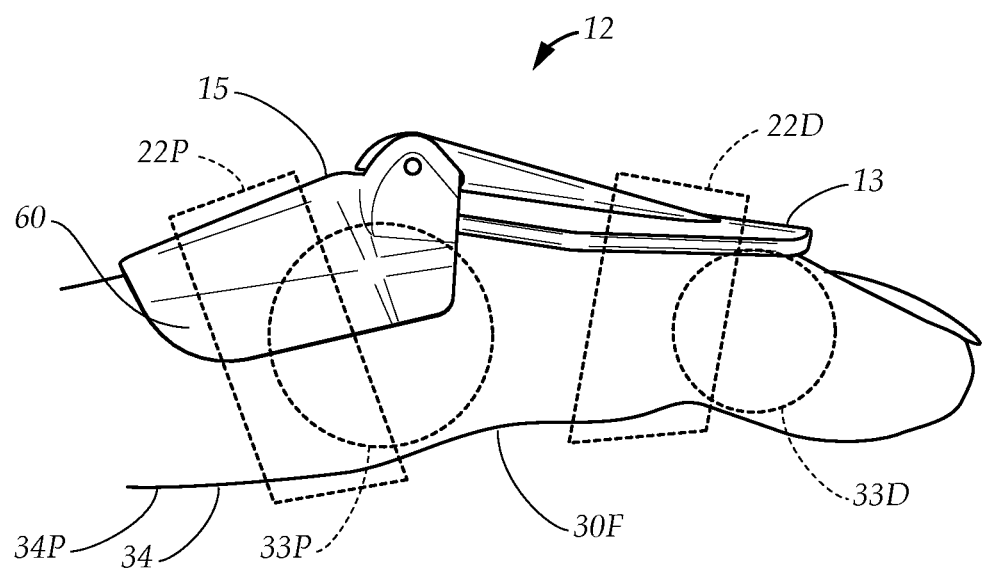
FIG. 13 is a side elevational view, similar to FIG. 11, showing the proximal strap and distal strap in relation to the finger (shown in phantom lines).

Referring to FIGS. 6 and 7, the straps 22 are preferably configured such that one end thereof is permanently attached to the sheath 80, and a free end thereof is then fully opposite from the sheath 80. Now, referring to FIG. 13, the free end of the proximal strap 22P is wrapped around inferior side 30F of the proximal part 34 of the finger 30 between the proximal end 34P and the PIP joint 33P, around and over the proximal segment 15 of the guard core 12, and then secured onto itself. Also, the free end of the distal strap 22D is wrapped around the inferior side 30F of the distal part 32 between the PIP joint 33P and the DIP joint 33D, around and over the distal segment 13, and then secured onto itself. Note that while the guard core 12 is securely anchored to the proximal part 34 of the finger by the virtue of the side extensions 60 that extend alongside the finger, up to and alongside the PIP joint 33P, the sides of the distal part of the finger are not covered by the distal segment, which only extends on the superior side 30S of the finger. Accordingly, significant freedom to play a sport is provided, as well as the ability to provide ball control and ball handling as if the guard were not being worn. The anchoring of the guard on the proximal segment, however, still provides significant protection against lateral forces, and effectively resists lateral twisting movement of the guard at the distal end. Even upon a hit on the distal end of the finger, such twisting that might otherwise lead to a sideway break of the finger is prevented. In particular, sideways movement of the distal segment is prevented by the anchoring of the proximal segment to the proximal part of the finger by virtue of the robustness of the hinge assembly and the resulting strong connection between the distal segment and the proximal segment. Thus, the distal segment need only attach onto the superior side of the finger and need not extend around the sides of the distal part of the finger. Thus, the goal of providing maximum protection to the finger with an optimal arrangement of minimal mass, while maximizing natural game play and ball handling is effectively achieved by the configuration discussed hereinabove.

It is understood that when an element is referred hereinabove as being "on" another element, it can be directly on the other element or intervening elements may be present therebetween. In contrast, when an element is referred to as being "directly on" another element, there are no intervening elements present.

Moreover, any components or materials can be formed from a same, structurally continuous piece or separately fabricated and connected.

It is further understood that, although ordinal terms, such as, "first," "second," "third," are used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

Spatially relative terms, such as "beneath," "below," "lower," "above," "upper" and the like, are used herein for ease of description to describe one element or feature's relationship to another element(s) or feature(s) as illustrated in the figures. It is understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device can be otherwise oriented (rotated 90 degrees or at other orientations) and the spatially relative descriptors used herein interpreted accordingly.

Example embodiments are described herein with reference to cross section illustrations that are schematic illustrations of idealized embodiments. As such, variations from the shapes of the illustrations as a result, for example, of manufacturing techniques and/or tolerances, are to be expected. Thus, example embodiments described herein should not be construed as limited to the particular shapes of regions as illustrated herein, but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

In conclusion, herein is presented a guard for protecting a finger during athletic activity. The disclosure is illustrated by example in the drawing figures, and throughout the written description. It should be understood that numerous variations are possible, while adhering to the inventive concept. Such variations are contemplated as being a part of the present disclosure.

What is claimed is:

1. A guard configured to protect a finger while allowing finger mobility during athletic activity, the injured finger having a distal part, a proximal part, a fingertip on the distal part, a fingernail near the fingertip, a nail bed just proximal of the fingernail, a proximal interphalangeal joint between the distal part and proximal part, a superior surface and an inferior surface, the guard comprising:
   a core having a distal segment and a proximal segment, the proximal segment and distal segment each having a top surface and a bottom surface, the core adapted for receiving the superior surface of the finger along the bottom surfaces of the proximal and distal segments, the proximal segment has side extensions having rear side edges that substantially oppose each other, the proximal segment curves transversely downwardly toward the rear side edges, the distal segment has a distal end and a distal end edge at the distal end, the distal segment has forward side edges extending proximally from the distal end edge, the rear side edges at the proximal segment extend wider than the forward side edges at the distal segment, the distal segment adapted for receiving the distal part of said finger and the proximal segment adapted for receiving the proximal part of said finger, the distal segment extending on top of but not alongside the distal part of the finger, and extending toward the fingertip to substantially the nail bed; and
   a hinge assembly, located above the top surfaces of the proximal and distal segments, and positioned just distal of the proximal interphalangeal joint and the side edges of the proximal segment extending alongside the proximal part of the finger, the hinge assembly including a pair of brackets on the proximal segment having a flat bridge surface therebetween, and a fin rib attached to the distal segment and extending distally thereon, the fin rib extends between the brackets and protrudes upwardly from the top surface of the distal segment, centered between the forward side edges and tapering downwardly toward the top surface as it extends distally, the fin rib has a tongue that interacts with the bridge surface to limit movement of the hinge assembly such that the distal part reaches a maximum position where the bottom surfaces of the proximal part and distal part do not fully align but instead form an obtuse angle that thereby is adapted to prevent the finger from fully straightening.

2. The guard as described in claim 1, further comprising a sheath, fully encasing the core and hinge assembly, and further comprising a lower pad, extending under the hinge against the bottom surfaces of the proximal segment and distal segments only in a region where the proximal segment meets the distal segment.

3. The guard as described in claim 2, wherein the proximal segment has rear side edges, and the proximal segment has a proximal end and a fork split extending longitudinally from the proximal end, the fork split allowing the rear side edges to move away from each other, the proximal segment adapted for accommodating fingers of differing widths.

4. The guard as described in claim 3, wherein the fin rib includes a fin rib knuckle that extends between the brackets and has the tongue, wherein the fin rib is substantially centered on the top surface of the distal part, wherein the brackets and fin rib knuckle are together wider than the distal segment.

5. The guard as described in claim 4, wherein the forward side edges of the distal segment are narrower than the brackets of the hinge assembly.

6. A guard configured to protect a finger while allowing finger mobility during athletic activity, the injured finger having a distal part, a proximal part, a fingertip on the distal part, a fingernail near the fingertip, a nail bed just proximal of the fingernail, a proximal interphalangeal joint between the distal part and proximal part, a superior surface and an inferior surface, the guard comprising:
   a core having a distal segment and a proximal segment, the proximal segment and distal segment each having a top surface and a bottom surface, the core adapted for receiving the superior surface of the finger along the bottom surfaces of the proximal and distal segments, the proximal segment has side extensions having rear side edges that substantially oppose each other, the proximal segment curves transversely downwardly toward the rear side edges, the distal segment has a distal end and a distal end edge at the distal end, the distal segment has forward side edges extending proximally from the distal end edge, the rear side edges at the proximal segment extend wider than the forward side edges at the distal segment, the distal segment adapted for receiving the distal part of said finger and the proximal segment adapted for receiving the proximal part of said finger, the distal segment extending on top of but not alongside the distal part of the finger, and extending toward the fingertip to substantially the nail bed; and a hinge assembly, located above the top surfaces of the proximal and distal segments, and positioned just distal of the proximal interphalangeal joint and the side edges of the proximal segment extending alongside the proximal part of the finger, the hinge assembly including a pair of brackets extending upwardly from the top surface of proximal segment and having a flat bridge surface therebetween, and a fin rib attached to the top surface of the distal segment and extending distally thereon, the fin fib tapers downwardly toward the top surface of the distal segment as it extends toward the distal end of the distal segment, the fin rib extends between the brackets and protrudes upwardly from the top surface of the distal segment, centered between the forward side edges and tapering downwardly toward the top surface as it extends distally, the fin rib has a tongue that interacts with the bridge surface to limit movement of the hinge assembly such that the distal part reaches a maximum position where the bottom surfaces of the proximal part and distal part do not fully align but instead form an obtuse angle that thereby is adapted to prevent the finger from fully straightening, wherein the forward side edges of the distal segment are narrower than the brackets of the hinge assembly.

7. The guard as described in claim 6, wherein the proximal segment has rear side edges, and the proximal segment has a proximal end and a fork split extending longitudinally from the proximal end, the fork split allowing the rear side edges to move away from each other, the proximal segment adapted for accommodating fingers of differing widths.

8. The guard as described in claim 7, wherein the fin rib includes a fin rib knuckle that extends between the brackets and has the tongue, wherein the fin rib is substantially centered on the top surface of the distal part, wherein the brackets and fin rib knuckle are together wider than the distal segment.

9. The guard as described in claim 8, further comprising a sheath, fully encasing the core and hinge assembly, and further comprising a lower pad, extending under the hinge against the bottom surfaces of the proximal segment and distal segments only in a region where the proximal segment meets the distal segment.

10. A finger guard method for employing a device configured to protect a finger while allowing finger mobility during athletic activity, the finger having a proximal end and a fingertip furthest distally, a proximal part and a distal part, a proximal interphalangeal joint between the proximal part and distal part, a distal interphalangeal joint on the distal part between the proximal interphalangeal joint and the fingertip, a fingernail near the fingertip, and a nail bed just proximal of the fingernail, the finger having a superior surface and an inferior surface, comprising the steps of:

providing the device comprising a guard, the guard having a distal segment, a proximal segment, and a hinge assembly between the proximal segment and distal segment, the proximal segment having a top surface and a bottom surface, the distal segment having a top surface and a bottom surface, the hinge assembly attached to the top surface of the distal segment and proximal segment, comprising the steps of:

securing the guard to the finger by extending the proximal part of the finger within the proximal segment and the distal part of the finger under the distal segment with the hinge assembly more proximal than the proximal interphalangeal joint and with the distal end near the nail bed;

protecting the finger while engaging in athletic activity by allowing the finger to bend but not fully straighten by allowing the distal segment to move between a minimum position with respect to the proximal segment, and a maximum position with respect to the proximal segment where the distal assembly is at an obtuse angle with the proximal segment.

11. The finger guard method as recited in claim 10, wherein the proximal segment has side extensions that curve downwardly from the top surface of the proximal segment, wherein the step of securing the guard to the finger by extending the proximal part of the finger within the proximal segment further comprises anchoring the finger guard to the proximal part of the finger by extending the proximal part of the finger between the sides extensions while only covering the top of the superior surface of the distal segment by the distal part, and wherein the step protecting the finger further comprises resisting lateral twisting of the guard at the distal part by securely holding the proximal part of the finger by the proximal segment.

12. The finger guard method as recited in claim 11, wherein the guard includes a sheath that fully encloses the core, and a proximal and distal strap attached to the sheath, and wherein the step of securing the guard to the finger further comprises the steps of securing the proximal strap by wrapping the proximal strap around the inferior surface of the proximal part of the finger between the proximal end and the proximal interphalangeal joint and fastening the proximal strap onto itself, and securing the distal strap by wrapping the distal strap around the inferior surface of the distal part of the finger between the proximal interphalangeal joint and the distal interphalangeal joint, and fastening the distal strap onto itself.

13. The finger guard method as recited in claim 12, wherein the hinge assembly includes a pair of brackets on top of the top surface of the proximal segment and a fin rib attached to the top surface of the distal segment and having a knuckle that extends between the pair of brackets; and wherein the step of providing the guard further comprises positioning the hinge assembly on the top surface of the proximal segment inwardly of the side extensions for preventing interference with adjacent fingers while engaging in athletic activity.

14. The finger guard method as recited in claim 13, wherein the step of protecting the finger further comprises cushioning the finger from the hinge assembly and reducing shock transmission to the finger by providing and extending a pad under the hinge assembly, the pad only extending in a region where the bottom surface of the proximal segment meets the bottom surface of the distal segment.

\* \* \* \* \*